United States Patent [19]

Schroeter et al.

[11] 4,061,652

[45] Dec. 6, 1977

[54] URETHANES OF HYDROXYBENZOTRIAZOLES

[75] Inventors: Siegfried H. Schroeter; Daniel R. Olson, both of Schenectady, N.Y.

[73] Assignee: General Electric Company, Schenectady, N.Y.

[21] Appl. No.: 626,490

[22] Filed: Oct. 28, 1975

[51] Int. Cl.$^2$ .......................................... C07D 249/20
[52] U.S. Cl. ..................... 260/308 B; 260/45.8 NT; 560/24; 560/132
[58] Field of Search ..................................... 260/308 B

[56] References Cited

U.S. PATENT DOCUMENTS

| | | | |
|---|---|---|---|
| 3,280,138 | 10/1966 | Molnar et al. | 260/308 B |
| 3,616,367 | 10/1971 | Zunker | 204/159.16 |
| 3,766,205 | 10/1973 | Heller et al. | 260/308 B |

FOREIGN PATENT DOCUMENTS

| | | | |
|---|---|---|---|
| 974,713 | 11/1964 | United Kingdom | 260/308 B |

*Primary Examiner*—Paul M. Coughlan, Jr.
*Attorney, Agent, or Firm*—William A. Teoli; Joseph T. Cohen; Jerome C. Squillaro

[57] ABSTRACT

Urethanes of hydroxybenzotriazoles and hydroxybenzophenones which can be chemically modified upon heating have been found useful in imparting weather resistance to plastic substrates when applied as part of a UV curable resin which can be subsequently heated after cure. UV curable resins containing such urethanes and the use of such resins to treat thermoplastic substrates are also described.

3 Claims, No Drawings

URETHANES OF HYDROXYBENZOTRIAZOLES

The present invention relates to urethane derivatives of hydroxybenzotriazoles and hydroxybenzophenones. More particularly, the present invention relates to the use of such urethanes in UV curable organic resins, and the employment of such UV curable organic resins to treat thermoplastic substrates to provide composites having improved weathering resistance.

Prior to the present invention, the plastics industry was constantly looking for suitable UV stabilizers to treat a wide variety of thermoplastics, such as polycarbonates, polyphenylene oxides, etc., in various applications in which the plastic parts were exposed to sunlight and other atmospheric conditions. Those skilled in the art know, for example, that after an extended period of exposure, thermoplastics, such as polycarbonates, tend to acquire a yellow color which reduces the attractiveness of the finished part and its utility. Efforts to improve the weatherability and sunlight resistance of thermoplastics have been successful, by treating the surface of the thermoplastic with an organic resin containing a UV stabilizer, such as a benzotriazole or a hydroxybenzophenone. A heat cure of the organic resin or the production of a preformed thermoplastic sheet containing the stabilizer can be used to provide a protective coating for the thermoplastic sheet. The preformed thermoplastic sheet containing the stabilizer has to be secured to the thermoplastic substrate by use of an adhesive or by the use of heat and pressure. Recently, a wide variety of UV curable acrylic and polyester resins have been developed which can be painted onto the surface of a variety of substrates, including plastic substrates, and cured within a minute or less under ultraviolet light. However, it has been found that if a UV stabilizer, such as a hydroxybenzophenone or hydroxybenzotriazole, is employed in the UV curable resin, the stabilizer absorbs a major portion of the UV light and interferes with the cure of the UV curable resin rendering the process economically unattractive.

As shown by British patent specification No. 974,713, substituted 2-phenylbenzotriazole compounds, such as 2-(2-alkenyloxyphenyl)-benzotriazole, can be thermally decomposed after a period of about 1 hour or more at a temperature of 180°–220° C to yield a 2-(2-hydroxyphenyl) benzotriazole which can be employed as a UV stabilizer. Although valuable results can be obtained by the use of such substituted 2-phenylbenzotriazoles, a relatively high decomposition temperature and an extended time is required to effect the liberation of the "UV filter" which drastically limits the use of these materials by plastics industry.

The present invention is based on the discovery that certain urethanes of hydroxybenzotriazoles and hydroxybenzophenones, as shown below by formula 1, can be used in UV curable organic resins, such as acrylic resins, in combination with certain catalysts, such as dibutyltin dilaurate, to provide cured films on thermoplastic substrates. The hydroxybenzotriazole or hydroxybenzophenone can thereafter be liberated at temperatures of about 130° C during standard thermoplastic sheet drying periods. The organic urethanes which can be used in the practice of the invention, which can be converted in-situ to UV stabilizers in a subsequent heating step, have the formula

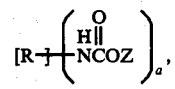

where R is an aliphatic or aromatic organic radical, $a$ is an interger equal to 1 or 2, when $a$ is 1, R is monovalent, when $a$ is 2, R is divalent and Z is an aromatic organic radical selected from the class consisting of

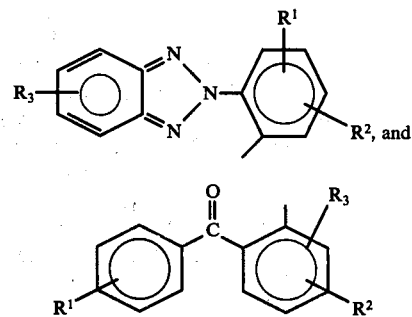

wherein $R^1$, $R^2$ and $R^3$ can be the same or different monovalent radicals selected from the class consisting of alkyl radicals, alkoxy radicals, halogen radical and hydrogen.

Radicals included by R are more particularly $C_{(6-13)}$ aromatic hydrocarbon radicals, such as phenyl, tolyl, xylyl, naphthyl, phenylene, tolylene, xylylene, naphthylene, etc., and halogenated derivatives thereof, such as chlorophenyl, bromotolyl, etc; $c_{(1-12)}$ alkyl radicals, such as methyl, ethyl, propyl, butyl, pentyl, hexyl, heptyl, octyl, etc.; methylene, ethylene, propylene, butylene, etc., and halogenated derivatives thereof, such as chloropropyl, bromobutyl, etc. Radicals included by $R^1$, $R^2$ and $R^3$ are all of the aforementioned alkyl radicals included by R and alkoxy radicals, such as methoxy, propoxy, butoxy, etc. In addition to the organic urethanes of formula (1), polymeric urethanes derived from polyesters, polyethers, polyglycols, etc., also can be used.

Included by the aryl urethanes of formula 1 are substituted benzotriazoles, such as 2-(2H-benzotriazol-2-yl)-4-t-octylphenyl N-ethylcarbamate,
2-(2H-benzotriazol-2-yl)-4-t-octylphenyl N-phenylcarbamate,
2-(2H-benzotriazol-2-yl)-4-t-octylphenyl N-butylcarbamate,
2-(2H-benzotriazol-2-yl)-4-methylphenyl N-ethylcarbamate,
2-(2H-benzotriazol-2-yl)-4-methylphenyl N-phenylcarbamate,
2-(2H-benzotriazol-2-yl)-4-methylphenyl N-butylcarbamate,
2-(2H-benzotriazol-2-yl)-4,6-di-t-pentylphenyl N-ethylcarbamate,
2-(2H-benzotriazol-2-yl)-4,6-di-t-pentylphenyl N-phenylcarbamate,
2-(2H-benzotriazol-2-yl)-4,6-di-t-pentylphenyl N-butylcarbamate,
2-(2H-5-chlorobenzotriazol-2-yl)-4-methyl-6-t-butylphenyl N-butylcarbamate,
2-(2H-5-chlorobenzotriazol-2-yl)-4-methyl-6-t-butylphenyl N-ethylcarbamate, 2-(2H-5-chlorobenzotriazol-2-yl)-4-methyl-6-t-butylphenyl N-phenylcarbamate,
2-(2H-5-chlorobenzotriazol-2-71)-4,6-di-t-butylphenyl N-ethylcarbamate,
2-(2H-5-chlorobenzotriazol-2-yl)-4,6-di-t-butylphenyl N-butylcarbamate and
2-(2H-5-chlorobenzotriazol-2-yl)-4,6-di-t-butylphenyl N-phenylcarbamate Also included by the aryl urethanes of formula 1 are substituted benzophenones, such as 2-benzoyl-4-dodecyloxyphenyl N-ethylcarbamate,
2-benzoyl-4-dodecyloxyphenyl N-butylcarbamate,
2-benzoyl-4-dodecyloxyphenyl N-phenylcarbamate,
2-benzoyl-4-methoxyphenyl N-phenylcarbamate,
2-benzoyl-4-methoxyphenyl N-butylcarbamate,
2-benzoyl-4-methoxyphenyl N-ethylcarbamate,
2-benzoyl-4-n-octoxyphenyl N-ethylcarbamate,
2-benzoyl-4-n-octoxyphenyl N-butylcarbamate,
2-benzoyl-4-n-octoxyphenyl N-phenylcarbamate,
2-benzoyl-4-dodecyloxyphenyl N-4-methylphenylcarbamate,
2-benzoyl-4-methoxyphenyl N-3-methylphenylcarbamate,
2-benzoyl-4-n-octoxyphenyl N-4-methoxyphenylcarbamate,
2-(4-methylbenzoyl)-4-methoxyphenyl N-phenylcarbamate and
2-benzoyl-4-ethoxyphenyl N-1-naphthylcarbamate.

In addition to the aryl urethanes of the present invention, there is also included UV curable organic resins, such as acrylic resins, polyester resins, epoxy resins, polythiolenes, etc., containing 0.1 to 10% by weight of the above described aryl urethanes, and 0.01 to 1% by weight of a decomposition catalyst, where the total weight of the organic resin, the aryl urethane, and the catalyst is equal to 100%.

The acrylic resins which can be employed in the practice of the present invention are, for example, mixtures of olefinically unsaturated organic monomers, such as methyl methacrylate, in combination with polymers, such as polymethylmethacrylate, polymethylacrylate, polyethylacrylate, etc. The proportion of the aforementioned olefinically unsaturated monomer and polymer in the acrylic resin can vary widely. For example, there can be utilized from about 30 to 90 parts of olefinically unsaturated monomer, per part of acrylic resin.

In addition to the above described acrylic resins, there also can be used in the practice of the present invention to make the UV curable organic resins, polyesters, such as reaction products of aliphatic dicarboxylic acids including, for example, fumaric or maleic acid with glycols, such as ethyleneglycol, propyleneglycol, neopentylglycol, etc., and mixtures thereof.

Epoxy resins also can be used as the organic resin and include monomeric, dimeric, oligomeric or polymeric epoxy material containing one or a plurality of epoxy functional groups. For example, reaction products of bis phenol-A and epichlorohydrin, or the epichlorohydrin with phenol-formaldehyde resins, etc. Further examples are shown on Vol. 6, 1967, Interscience Publishers, New York, pp. 209-271 of the Encyclopedia of Polymer Science and Technology. Other organic resins can be in the form of mixtures of polyolefin and polythiols, such as shown by Kehr et al, U.S. Pat. Nos. 3,697,395 and 3,697,402. Photoinitiators which can be used to effect cure of the organic resins include benzophenone, benzoin ethers, quinones, such as t-butylnaphthoquinone, ketones, such as Michler's Ketone, etc. Also, dyes, pigments, fillers and other additives.

Catalysts which can be used in combination with the aryl urethanes of the present invention to promote their decomposition in the UV curable resins are, for example, tertiary amines, phosphines titanium esters, etc., and mixtures thereof. For example, there can be used triethylene diamine, triethyl amine, benzyl dimethyl amine, zinc octoate, Fe(III) acetyl-acetonate, Mn(III) acetyl-acetonate, V(III) acetyl-acetonate, dibutyltin dilaurate, isopropyl titanate, butyl titanate, Mn(III) acetyl-acetonate/triethyl amine, etc.

The aryl urethanes of the present invention can be made by standard procedures employing the corresponding hydroxybenzophenone or hydroxybenzotriazole with an appropriate organic isocyanate or diisocyanate in the presence of a catalyst, such as triethylene diamine, in an organic solvent, for example, methylene chloride. The mixture can be stirred under ambient conditions for an extended period of time, such as 10 to 100 hours. The product can be recovered by evaporation of volatiles followed by crystallized the residue from an aliphatic hydrocarbon, such as hexane. Included by the hydroxybenzotriazoles which can be used to produce the aryl urethanes of the present invention are, for example, 2-(3'-t-butyl-2'-hydroxy-5'-methylphenyl)-5-chlorobenzotriazole
2-(3',5'-ditert-butyl-2'-hydroxyphenyl)-5-chlorobenzotriazole
2-(3',5'-di-t-pentyl2'-hydroxyphenyl)-benzotriazole Included by the hydroxybenzophenones which can be used in the practice of the present invention to produce the aryl urethanes are, for example, 2-hydroxy-4-methoxybenzophenone
2-hydroxy-4-methoxy-4'-methylbenzophenone
2,2'-dihydroxy-4-methoxybenzophenone
2-hydroxy-4-methoxy-4'-methylbenzophenone
2-hydroxy-4-ethoxybenzophenone
2,2'-dihydroxy-4-butoxybenzophenone
2-hydroxy-4-n-heptoxybenzophenone
2,2'-dihydroxy-4,4'-dimethoxybenzophenone
2-hydroxy-4-n-octoxybenzophenone
2,2'-dihydroxy-4-octoxybenzophenone
2-hydroxy-4-methoxy-2'-carboxybenzophenone
2-hydroxy-4-methoxy-5-sulfonic acid benzophenone
2-hydroxy-4-acetadecyloxybenzophenone
2,2'-dihydroxy-4,4'-dimethoxy-5-sulphobenzophenone-Na
2-hydroxy-5-chlorobenzophenone Some of the organic isocyanates and organic diisocyanates, which can be used to produce the above described aryl urethanes, are organic isocyanates, such as phenyl isocyanate, tolyl isocyanate, hexamethylene diisocyanate, isophorone diisocyanate, toluene diisocyanate, p,p'-diphenylmethane diisocyanate and trimethylhexamethylene diisocyanate.

The above described UV curable resins can be applied by standard procedures, such as by a screen coater, a roller coater, painting, etc., onto the surface of various thermoplastic sheets, for example, polycarbonate sheets, polyphenyleneoxide sheets, polystyrene, etc.

The application of the UV curable resin can become 0.2 to 3 mils to provide for an adequate stabilizing effect in the cured film.

Cure of the organic resin can be achieved by the use of a standard UV lamp as a medium pressure mercury are, a fluorescent light tube, a Xenon flash lamp, laser, carbon arc, etc.

Another feature of the present invention are thermoplastic composites in the form of a thermoplastic sheet containing the cured resin film containing the organic urethane. These composites can be heat treated, such as by drying at temperatures in the range of about 130° C for 3 to 15 hours, to effect the breakdown of the aryl urethane and the liberation of the hydroxybenzotriazole or hydroxybenzophenone stabilizer.

In order that those skilled in the art will be better able to practice the present invention the following examples are given by way of illustration and not by way of limitation. All parts are by weight.

EXAMPLE 1

A solution of 7.64 parts of 2-hydroxy-4-dodecyloxybenzophenone, 2.7 parts of ethyl isocyanate and 0.05 part of triethylene diamine in 10 parts of dry methylene chloride was stirred at room temperature for 100 hours. There was obtained 4.4 parts which represented a yield of about 49% of 2-benzoyl-4-dodecyloxyphenyl N-ethyl carbamate, having a m.p. of 70°–72°, upon evaporation of the volatiles and recystallization from hexane. The identity of the product was confirmed by infrared spectrum and elemental analysis.

EXAMPLE 2

A solution of 12.92 parts of 2-(2'-hydroxy-5'-t-octylphenyl)-benzotriazole, 7.86 parts of phenyl isocyanate, 0.05 parts of triethylene diamine and 20 parts of methylene chloride was stirred at room temperature for 48 hours. Upon evaporation of the solvent there was obtained, by recrystallization of the residue from an ethyl acetate-hexane solution, 85% or 15.1 parts of 2-(2H-benzotriazol-2-yl-4-t-octylphenol) N-phenyl carbamate. The identity of the product was confirmed by its m.p. of 165°–175° C. elemental analysis and its infrared spectra.

EXAMPLE 3

A mixture was stirred 24 hours at room temperature consisting of a solution of 12.9 parts of 2-(2'-hydroxy-5'-t-octylphenyl)-benzotriazole, 4.49 parts of ethyl isocyanate, 0.05 parts of triethylene diamine and 20 parts of methylene chloride. Evaporation of the solvent, followed by recrystallization of the residue from an ethyl acetate-hexane mixture, gave 11.5 parts or a 73% yield of 2-(2-benzotriazol-2-yl)-4-t-octylphenyl N-ethyl carbamate, having a melting point of 152°–154° C. The identity of the product was confirmed by its infrared spectra and elemental analysis.

EXAMPLE 4

A film was cast from a methylene chloride solution of a mixture of 4.37 parts of 2-benzoyl-4-dodecyloxyphenyl N-ethyl carbamate, 0.19 parts of dibutyltin dilaurate and 120 parts of Elvacite 2042, a commercial high molecular weight polyethylmethacrylate, of the E. I. duPont de Nemours and Company. After the solvent had evaporated, the resultant film was floated from the glass with water. The film was cut into strips which were suspended in a 130° even for various amounts of time. The heated strips were then dissolved in chloroform and quantitatively analyzed by ultraviolet spectroscopy to determine weight percent of regenerated UV screen in the various strips based on the amount of absorption at 327 nm. It was found that the unheated film showed no absorption and, therefore, was free of the 2-hydroxy-4-dodecyloxybenzophenone. However, after about 60 minutes at 130° C, ⅔ of the aryl urethane has broken down to give the aforementioned UV absorber. After about 2 hours, almost 4/5 of the aryl urethane has reverted back to the 2-hydroxy-4-dodecyloxybenzophenone. A 90% conversion had been effected after 200 minutes. Those skilled in the art would know that, had the aforementioned film been employed as a protective coating on the surface of a polycarbonate sheet, an equivalent conversion of the aryl urethane to the UV stabilizer would have resulted during a standard drying cycle which is effected after at least 3 hours at a temperature of at least 130° C.

EXAMPLE 5

A resin composition within the scope of the present invention was prepared by blending together 40 parts by weight of a polymethylmethacrylate having a molecular weight of about 12,000, 60 parts by weight of methyl methacrylate, 1 part by weight of benzoin ethyl ether, 3 parts by weight of 2-benzoyl-4-dodecyloxyphenyl N-ethylcarbamate and 0.2 part by weight of dibutyltin dilaurate and 0.5 part of paraffin wax. The resin mixture was then applied to a thickness of about 2 mils onto a polycarbonate sheet and exposed to ultraviolet light. The degree of cure of the resin was measured by measuring the weight loss of the monomer in weight percent from the cured resin after baking for a period of 1 hour at 150° C. It was found that substantially the same conversion of monomer to the cured film was achieved with the urethane and without the urethane. However, when an equal weight percent of Eastman DOBP, a commercial hydroxybenzophenone useful as a UV stabilizer, was employed in the resin, the resin formulation did not cure. For example, after 6 minutes exposure under UV, the resin containing the commercial UV absorber lost about 16% by weight of unreacted methylmethacrylate while the resin containing the aryl urethane of the present invetnion lost only 5% by weight.

EXAMPLE 6

The above described UV curable resin of the present invention containing the urethane was applied to a polycarbonate sheet and then cured. The resulting composite was then heated at 3 hours at 130° C to convert the urethane to the corresponding UV stabilizer. The coated sheet was then exposed to intense accelerated weathering under UV irradiation for 400 hours. The aforementioned procedure was also repeated except that a resin was used to coat a polycarbonate sheet which was free of an organic urethane of the present invention. It was found that the polycarbonate sheet, treated with the resin composition of the present invention, showed no color while the polycarbonate sheet, treated with a UV curable composition free of the organic urethane, showed an intense yellow color having a yellow index value of at least 10. This procedure established that the resin composition of the present invention can be employed to impart valuable stabilization to various thermoplastic sheets.

EXAMPLE 7

The procedure of Example 4 was repeated except that it contained 4.26 parts of 2-(2-benzotriazol-2-yl)-4-t-octylphenyl N-ethylcarbamate of Example 3. It was found that about ⅔ conversion of the carbamate to the hydroxybenzotriazole was effected after heating the film about 20 minutes at 130° C. Almost complete conversion to the UV stabilizer was achieved after about 60 minutes at 130° C which amounted to about 95% based on the weight of the carbamate.

EXAMPLE 8

The procedure of Example 5 was repeated except that a UV curable organic resin was prepared containing 3 parts by weight N-ethylcarbamate of Example 3 and 0.2 part of dibutyltin dilaurate. Substantially similar results were obtained with the UV curable resin as that shown in Example 5.

The above results shown that the polymer organic urethane can provide effective UV stabilization when used in accordance with the practice of the invention.

EXAMPLE 9

An organic urethane is prepared by effecting reaction between a polyester reaction product of ethylene glycol, glycerol, adipic acid and phthalic acid having a molecular weight of about 800, and a hydroxyl functionality of 5, with 5.5 moles of hexamethylene diisocyanate. The resulting multifunctional polyisocyanate is then reacted with about 5.0 moles of 2-(2′-hydroxy-5′-t-octylphenyl)-benzotriazole to produce of polymeric organic urethane within the scope of the present invention substantially free of aromatic hydroxy functionality based on its IR spectrum.

A mixture of 10 parts of the above polymeric urethane and 0.2 parts of dibutyltin dilaurate is heated about 3 hours at a temperature of 130° C. It is found that the above hydroxy benzotriazole is released to a significant degree based on IR absorbtion.

Although the above examples are limited to only a few of the very many organic urethanes or UV curable organic resins which can be employed in the present invention, it should be understood that the present invention is directed to a much broader class of such materials as shown by formula (1) and the description preceding these examples.

What we claim as new and desire to secure by Letters Patent of the United States is:

1. Organic urethanes of the formula,

where R is a member selected from the group consisting of a $C_{(1-12)}$ aliphatic hydrocarbon radical, a $C_{(6-13)}$ aromatic hydrocarbon radical, and halogenated derivatives thereof, "a" is an integer equal to 1 or 2, and when a is 1, R is monovalent, and when a is 2, R is divalent, Z is an aromatic organic radical having the formula,

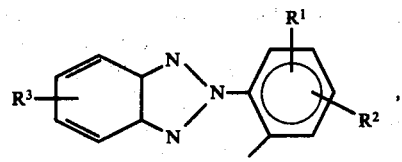

where $R^1$, $R^2$, and $R^3$ can be the same of different monovalent radicals selected from the group consisting of $C_{(1-12)}$ alkyl radicals, $C_{(1-4)}$ alkoxy radicals, halogen and hydrogen.

2. 2-(2-benzotriazol-2-yl)-4-t-octylphenyl N-phenylcarbamate.

3. 2-(2-benzotriazol-2-yl)-4-t-octylphenyl N-ethylcarbamate.

* * * * *